United States Patent [19]
Halford et al.

[11] 3,971,370
[45] July 27, 1976

[54] TONGUE AND JAW POSITIONING ARTICLE

[76] Inventors: George C. Halford; Robert E. Michael, both c/o Halbrand, P.O. Box 272, Willoughby, Ohio 44094

[22] Filed: Oct. 30, 1969

[21] Appl. No.: 872,499

[52] U.S. Cl. .............................................. 128/136
[51] Int. Cl.² ............................................ A61F 5/56
[58] Field of Search ................... 128/132, 136, 269; 272/57; 108/359

[56] References Cited
UNITED STATES PATENTS

| | | | |
|---|---|---|---|
| 2,408,735 | 10/1946 | Claflin | 128/359 |
| 2,491,274 | 12/1949 | McNeill | 128/269 |
| 2,595,462 | 5/1952 | Johnson | 128/359 |
| 3,228,398 | 1/1966 | Leonard et al. | 128/269 |
| 3,324,855 | 6/1967 | Heimlich | 128/269 |
| 3,508,547 | 4/1970 | Deuschle | 128/269 |

*Primary Examiner*—Lawrence Charles

[57] ABSTRACT

The article of this disclosure is to be used to prevent injury to persons who may be subject to periodic or other types of seizures in which grinding of the teeth, of the jaws, and possible biting of the tongue such as may occur in epileptic seizures, electro-convulsive therapy, shock or related voluntary or involuntary action of the jaws so as to prevent injury resulting therefrom. The article of the invention includes a specifically designed block of material having certain characteristics of resistance to penetration of the teeth in conjunction with a handle arranged in the block so as to increase the resistance to biting through the same, all of the various elements being designed to prevent swallowing of the block, yet facilitate supplying the same by reason of the ability to maintain cleanliness and also to facilitate administration of suitable medication where desired since the jaws are not closed against such administration.

5 Claims, 3 Drawing Figures

INVENTORS.
GEORGE C. HALFORD
BY ROBERT E. MICHAEL
Robb & Robb
attorneys

TONGUE AND JAW POSITIONING ARTICLE

The invention hereof comprises a block of expanded polyethylene plastic material of generally rectilinear form, having a density of approximately 6 pounds or more and preferably not more than 9 pounds per cubic foot, and of such a size as to be susceptible of insertion in the mouth of a person between the teeth in the upper and lower jaws thereof, and simultaneously to engage the tongue whereby to prevent swallowing the same, a suitable handle being provided to manipulate the block in anticipation of such use where seizures are contemplated or observed as about to take place.

A primary object of the invention is to provide an article of suitable size which is carefully designed to facilitate the various ends sought, at the same time to resist the biting pressures which may be developed in the mouth of a person having a prevalent seizure condition, which pressure under some circumstances may be as high as 200 pounds per square inch, and also to virtually eliminate the probability of the article itself being swallowed which would certainly defeat the purpose thereof in the final analysis.

Another object of the invention is to provide an article arranged with a generally rectilinear block of expanded polyethylene plastic foam of such a configuration as will virtually absolutely prevent swallowing the same since it cannot readily strike the palate and/or uvula, may be inserted in various positions between the jaws to effectuate the purposes hereof, and be composed of materials which are capable of being packaged and being distributed in sanitary containers or packages, the materials likewise being non-toxic.

Another object of the invention is to arrange the handle which is availed of to support the block of material, thereon, in such a manner as to be merely co-extensive with the said block of material and yet so positioned as to obviate possible damage which may occur should the handle be fractured during use.

Other and further objects of the invention will be understood from a consideration of the specification appended hereto and disclosed in the drawing wherein.

DESCRIPTION OF THE INVENTION

Figure 1:
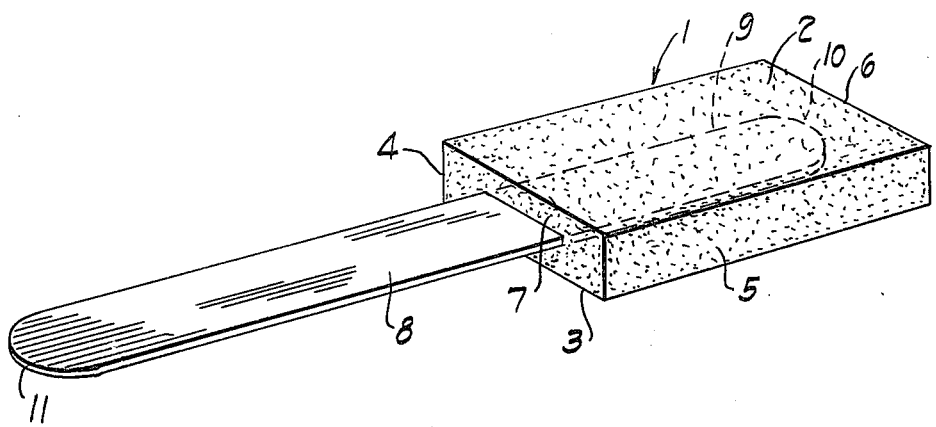
FIG. 1 is a perspective view of the article of this invention.

Referring now to FIG. 1, the article of this invention is shown as comprising a block of polyethylene plastic foam designated 1, being generally rectilinear in configuration, having an upper face 2, a lower face 3 opposite the same, sides 4 and 5, and ends 6 and 7.

It is noted that the block 1 hereof is preferably about 2¼ inches long, 1¼ inches wide, and about ½ inch in thickness.

Shown as extending into the interior of the block 1, is a handle 8, having the portion within the block designated 9, with a suitable rounded end 10 thereon.

It will be understood that the handle 8 may be comprised of wood or similar substance, in this instance a wood strip being disclosed, wherein the outer end thereof is formed with a rounded end section 11 thereon.

The portion of the handle 8 within the block 1 extends into the block substantially co-extensive therewith, and within preferably about ¼ inch of the end 6 of said block.

The handle 8 is cemented by suitable non-toxic material into a suitable opening formed in the block 1, so that it is to all intents and purposes virtually integral with said block.

As initially suggested, the block 1 is formed of expanded polyethylene foam, the density being calculated on the basis of weight, and preferably as so calculated about 6 pounds per cubic foot and not more than 9 pounds per cubic foot.

It is particularly noted that the density of the foam material is a very important factor in this invention, because it has been found that the density prescribed is such as to virtually entirely resist biting through of the same on the part of the patient or subject in whose mouth the article may be inserted, and in any event the positioning of the handle 8 as to the end 9 thereof within the block, is such as to be in effect additive to the resistance provided by the block against biting through the same.

Figure 2:
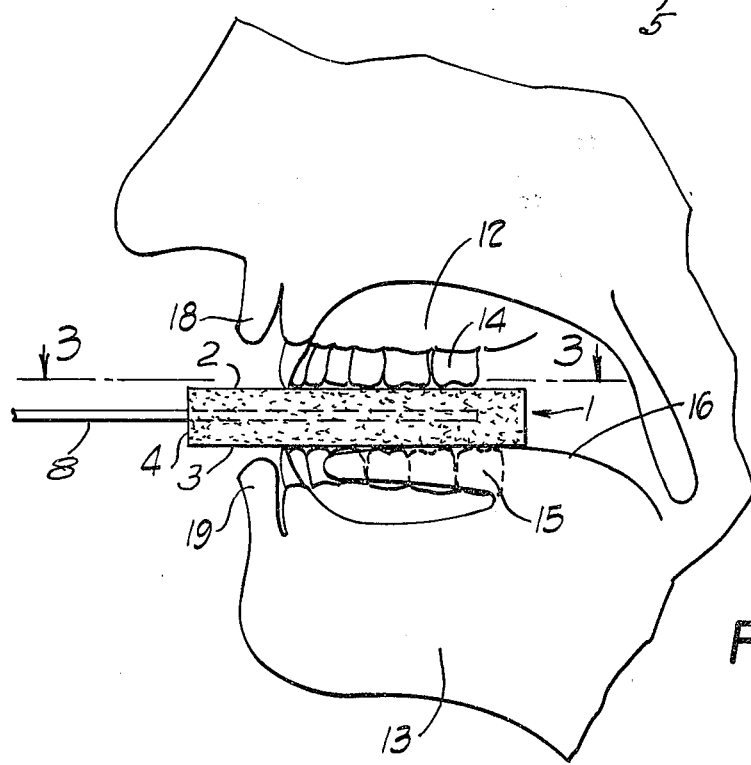
FIG. 2 is a fragmentary view, showing an article of this invention emplaced within a subject's mouth and between the jaws and teeth thereof.

This is disclosed in the other figures in the drawing, particularly FIG. 2, which shows the block 1 as being positioned between the upper jaw 12 and lower jaw 13 of the patient, and particularly of course between the teeth 14 and 15 respectively, with a substantial portion of the block in engagement with the tongue 16 of the subject, and yet the end 4 of the said block extends beyond the upper and lower lips 18 and 19 respectively.

With the article of this invention in place as indicated in FIG. 2, the patient or subject cannot bite through the foam block and in fact the harder the bite is exerted, the more pressure is likewise exerted upon the tongue so as to prevent swallowing the same as may be possible during seizures of various types including epileptic, electro-convulsive therapy and shock.

Figure 3:
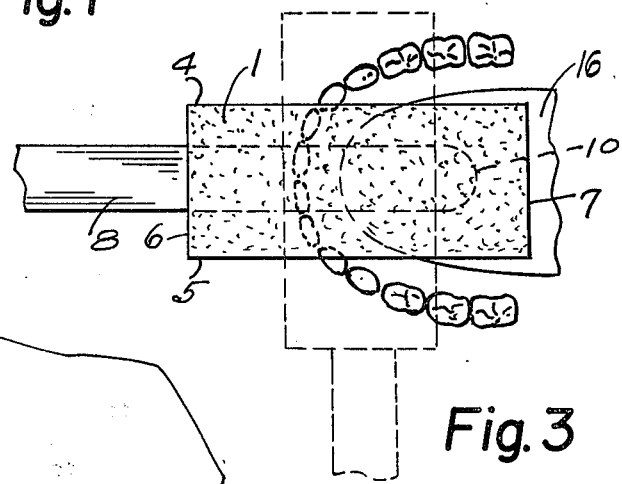
FIG. 3 is somewhat diagrammatic, illustrating further various positions which may be adopted for use of the article hereof.

Since under some circumstances it will not be possible to insert the article of this invention in the position shown in FIG. 2, as indicated in dotted lines in FIG. 3, the article may be inserted transversely of the jaw so to speak, extending across from side to side of the teeth therewithin and still a substantial portion of the block 1 extends over the tongue 16 so that it is maintained in a position virtually impossible for the subject to swallow.

It is of course understandable that various positions may be necessarily resorted to between the two positions disclosed where circumstances compel such positioning and still the effective nature of the article hereof is availed of to prevent grinding of the teeth by permitting them to penetrate or to at least depress to a certain extent or compress to a certain extent the material of the block, without permitting the biting through of the block, and yet pressure is exerted upon the tongue because of the size and arrangement of the respective parts.

It should be noted that the end 10 of the handle 8 is sufficiently far from the extremity or end 6 of the block 1 so that even if it is shattered to any extent, it will not be possible for the splinters or broken parts to come into contact or be swallowed by the subject.

Since the block 1 is of such a size and shape, rectilinear in this instance, and of substantial size, it is clear that it will be virtually impossible for anyone to swallow and thus result in further harm than is caused by the seizure itself. Further, the very size of the end and the rectilinear nature thereof will prevent the article from striking the palate and thus further insure against swallowing of the article hereof.

A substantial amount of experimentation has been resorted to in determining the various sizes and proportions as well as the shape of the article hereof, and the purposes have been explained as heretofore outlined with results being accomplished which are in all aspects satisfactory to provide for tongue and jaw positioning in seizures of the type which result from epileptic attacks, or like conditions.

We claim:

1. In a tongue and jaw positioning article of the class described, in combination, a block of relatively dense, rigid plastic foam for inserting in the mouth of a subject, said block being approximately the width of the tongue of such subject and a length to substantially overlie such tongue, said block extending between and outwardly of the teeth of the upper and lower jaws of such subject when emplaced therebetween, the thickness and density of the block normally preventing the teeth of such subject from penetrating the block to any substantial depth, and the teeth of such upper and lower jaws from interengaging when the block is in the position described, and a strip of much harder relatively thin and non-yieldable material, fixed in said block extending over a substantial portion of the area of the block whilst being confined therein, one end of said strip extending outwardly from the block to form a handle.

2. The combination as claimed in claim 1, wherein the block is of generally rectilinear configuration and formed of expanded polyethylene material.

3. The combination as claimed in claim 2, wherein the expanded polyethylene material comprises a foam having a density of approximately 6 to 9 pounds per cubic foot.

4. The combination as claimed in claim 1, wherein the strip of material is comprised of wood, the said other end terminating a short distance from the end of the block opposite the said one end.

5. The combination as claimed in claim 2, wherein the block is approximately 2¼ inches long, 1¼ inches wide, and ½ inch thick.

* * * * *